United States Patent

Nixon

[11] Patent Number: 5,100,426
[45] Date of Patent: Mar. 31, 1992

[54] CATHETER FOR PERFORMING AN ATHERECTOMY PROCEDURE

[75] Inventor: Jeddy D. Nixon, Houston, Tex.

[73] Assignee: FTS Engineering, Inc., Houston, Tex.

[21] Appl. No.: 386,998

[22] Filed: Jul. 26, 1989

[51] Int. Cl.⁵ ............................................. A61B 17/32
[52] U.S. Cl. ..................................... 606/170; 604/22; 606/159
[58] Field of Search ................... 604/22; 606/170, 169, 606/159; 128/804

[56] References Cited

U.S. PATENT DOCUMENTS

| | | | |
|---|---|---|---|
| 4,167,944 | 9/1979 | Banko | 606/170 |
| 4,598,710 | 7/1986 | Kleinberg et al. | 606/170 |
| 4,631,052 | 12/1986 | Kensey | 604/22 |
| 4,690,140 | 9/1987 | Mecca | 604/22 |
| 4,696,667 | 9/1987 | Masch | 604/22 |
| 4,804,364 | 2/1989 | Dieras et al. | 606/169 |
| 4,808,153 | 2/1989 | Parisi | 606/169 |
| 4,857,045 | 8/1989 | Rydell | 604/22 |

OTHER PUBLICATIONS

Article describing "Roto-Rooter" described in the Apr. 1988 issue of Popular Science.
Article taken from Houston Chronical newspaper dated Sunday, Jun. 25, 1989.

Primary Examiner—C. Fred Rosenbaum
Assistant Examiner—William Lewis
Attorney, Agent, or Firm—Vaden, Eickenroht, Thompson & Boulware

[57] ABSTRACT

A catheter for performing an atherectomy procedure to remove plaque from an artery is disclosed. The catheter includes a plaque cutting head having an outer shell of thin flexible material generally cylindrical in cross-section and shaped to engage plaque in an artery. The outer shell has a plurality of openings through which the plaque will enter the shell as the shell is forced against the plaque. A cutter rotates inside the shell to cut the plaque that enters into the shell into small pieces as the catheter is pushed through an artery. A motor drive elongated drive shaft rotates the cutter.

7 Claims, 2 Drawing Sheets

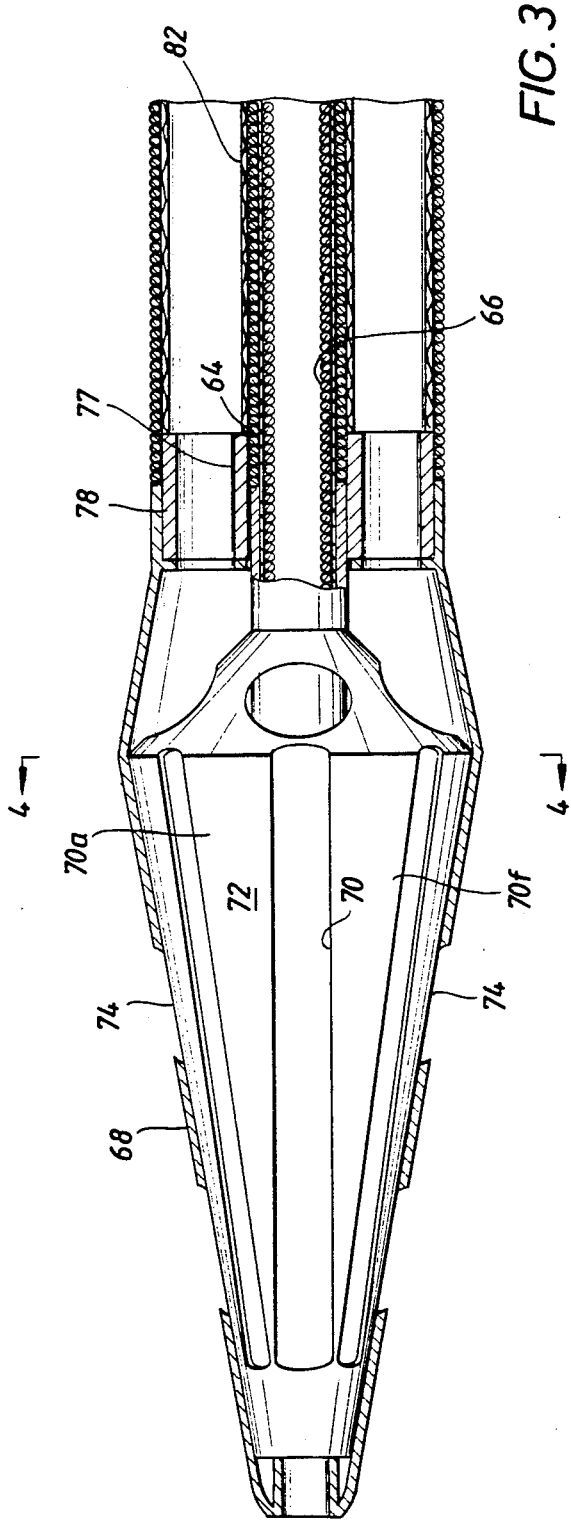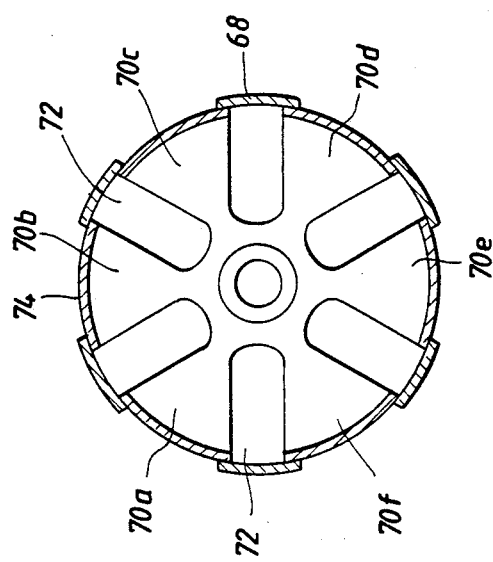

CATHETER FOR PERFORMING AN ATHERECTOMY PROCEDURE

This invention relates to catheters generally and in particular, to a catheter for performing an atherectomy procedure.

For many years a procedure called angioplasty has been used to open arteries clogged with plaque. The catheter carries a balloon to the location where the artery is clogged. The balloon is inflated to flatten the plaque against the vessel wall and form a larger opening through the artery. Angioplasty is widely accepted by the medical profession and these procedures have successfully saved or improved the quality of many lives for the past several years. It does have some problems however. Emerging statistics tend to show that treated vessels, veins, or arteries, though expanded, frequently revert to critical restrictive conditions.

Atherectomy is a procedure that utilizes a cutting tool to remove hardened atheroma from the lumen (channel) of arteries. Atheroma is a mass of plaque of degenerated, thickened arterial intima occurring in atherosclerosis. This is the condition in which deposits of plaque containing cholesterol lympoid materials and lipophages are formed and retained on the walls of arteries with great tenacity.

Thus, it is an object of this invention to provide a catheter for performing an atherectomy procedure that will cut the plaque from the walls of an artery into very small pieces and remove the plaque cuttings from the artery through a passageway in the catheter.

It is a further object of this invention to provide such a catheter that will leave the walls of the artery smooth to discourage and delay another build up of plaque.

It is a further object of this invention to provide such a catheter that will vibrate the cutting head of the catheter along the longitudinal axis of the artery to reduce the chances of the cutting head becoming stuck in the artery and to improve the cutting action of the cutting head.

It is a further object of this invention to provide such a catheter with a cutting head having an outer shell of thin flexible material having openings therein through which plaque will protrude when the outer shell is forced against the plaque and a cutter rotating in the outer shell to shave off the plaque that protrudes through the openings, said cutter being designed to close all of the openings when the cutter is in one position relative to the outer shell and to limit the openings that are open at any given time as the cutter rotates relative to the outer shell so that only a portion of the plaque is being severed from the wall of the artery at any given time thereby reducing the torque required to rotate the cutter.

It is another object and feature of this invention to provide such a catheter with a passageway extending from the cutting head to a location outside the patient and means to lower the pressure in the passageway below the ambient pressure in the artery so that blood will flow out of the patient through the passageway carrying the severed plaque with it.

It is another object and feature of this invention to provide a check valve in the passageway through which the blood flows out of the patient to allow the pressure to be increased in the passageway to stiffen the catheter when the catheter is being inserted into the artery.

It is a further object of this invention to provide such a catheter having a cutting head with an outer shell of thin flexible material having openings therein and a hollow cutter located inside the outer shell having a outside surface adjacent the inside surface of the outer shell, said cutter having openings positioned similarly to the openings in the outer shell so that the edges of the openings in the cutter combine with the edges of the opening in the outer shell like scissor blades to shear the plaque protruding into the outer shell from the wall of the artery.

These and other objects, features, and advantages of this invention will be apparent to those skilled in the art from a consideration of this specification including the attached drawings and appended claims.

FIG. 3 is another, and probably the preferred embodiment, of the cutting head of this invention.

FIG. 4 is a sectional view taken along line 10-10 of FIG. 3.

Figure 1:
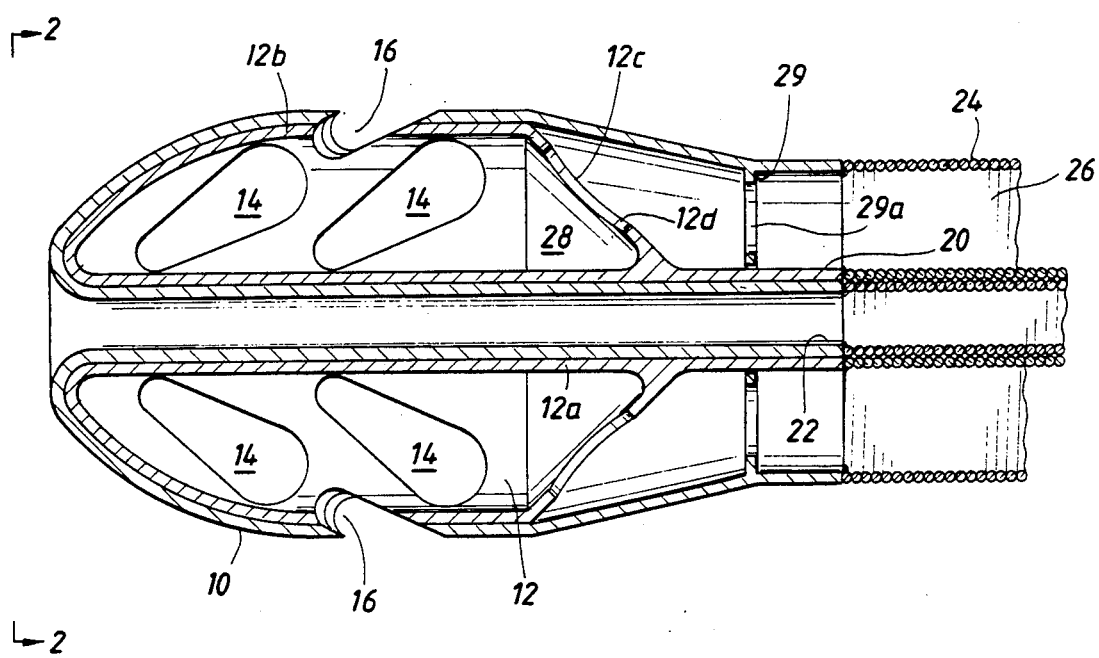
FIG. 1 is a side view partially in section and partially in elevation, of one embodiment of the cutting head of this invention, which is located at the forward end of the catheter.

The cutting head shown in FIG. 1 includes outer shell 10 and cutter 12 located inside the outer shell. The cutter includes central tubular section 12a and outer section 12b that encircles the central tubular section and is spaced therefrom except at the forward end where the two are connected. Inclined disc 12c extends between the central section and the rearward end of the outer section to connect the two and support the outer section.

The outer section of the cutter is shaped to match the shape of the outer shell and is positioned to be in sliding engagement with the outer shell when the outer shell is moved into engagement with the plaque in an artery. The outer shell is shown in the drawings to be about as thick as the outer section of the cutter, but, actually it will be much thinner about 0.001 inch. The cutter has a plurality of openings 14 in the outer section and the outer shell has a plurality of openings 18 that are positioned for the openings in the cutter to pass over the openings in the outer shell as the cutter is rotated. The edges of the openings in the cutter act as cutting blades that cross the openings in the outer shell in the manner shown in FIG. 2 and sever the plaque extending into the opening in the outer shell like scissors.

Figure 2:
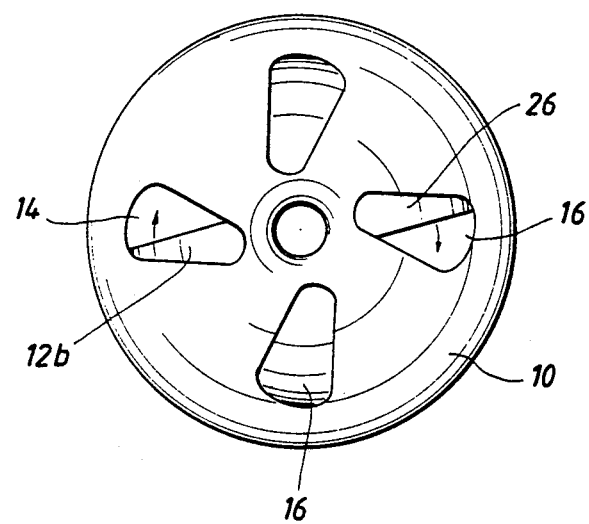
FIG. 2 is an end view of the cutting head of FIG. 1.

As shown in FIG. 2, plaque is being cut in only two openings in the outer shell. The other two openings that are shown in this figure are closed by the outer section of the cutter. This arrangement reduces the amount of torque necessary to rotate the cutter, which is a very important consideration since all of the parts making up the catheter are very small out of necessity.

Also, preferably, the outer section of the cutter can be positioned so that all of the openings in the outer shell are closed. This allows the catheter to be inserted into position in an artery without any exposed sharp edges.

Since the openings in the outer shell are spaced apart, to expose the entire inner surface to the cutter, the catheter is rotated slowly while not moving longitudinally until the openings have covered the entire circumference of the artery. The initial cutting of plaque occur at the forward openings. The rearward openings act as gauge cutters to remove the plaque closest to the wall of the vessel or artery.

Referring again to FIG. 1, the cutter is rotated by shaft 20, which is a flexible, tubular, member capable of transmitting the desired torque to the cutter head, such as a reinforced plastic tubing. Extending through the shaft and connected to the outer shell is tubular shaft guide 22, also made of reinforced tubing. The shaft guide must hold the outer shell from rotating with the cutter blades and to absorb the countertorque produced by the rotating cutter. The shaft guide is tubular to provide a central opening to receive the guide wire (not shown) that is usually inserted into the vein or artery prior to the insertion of the catheter.

Outer tube 24, also made of reinforced tubing, is also connected to the outer shell and absorbs some of the back-up torque. This tube has an inside diameter larger than the outside diameter of the shaft to provide annulus 26. In operation, the pressure in annulus 26 is reduced below ambient pressure to cause blood and the plaque cuttings to flow from inner annular chamber 28 of the cutter, through opening 12d in disc 12c, through opening 29a in spacer 29, through annulus 26, and out of the patient. Reducing the pressure in chamber 28 also helps pull the plaque into the openings in the cutter head.

The cutting head and catheter shown in FIGS. 3 and 4 have some additional features. Shaft 64 and cable guide 66 are connected to the cutter and outer shell, respectfully. The cutter in this embodiment has six elongated ribs 70a-70f as shown in FIG. 10. The ribs are spaced apart by longitudinally extending grooves 72. The edges of the ribs shave the plaque that protrudes into openings 74 in outer shell 68.

Shaft 64 is attached to the end of cylindrical stub shaft 76 of the cutter and to cylindrical piezo electric crystal 77 that extends over the stub shaft and is also attached to the stub shaft. Cylindrical piezo crystal 78 is cemented to vacuum tube 80 and to outer shell 68. Lead wire 82 extends along shaft 64 and supplies electricity to crystal (77) and lead wire 84 extends along vacuum tube 80 and supplies electricity to crystal 78. It is believed that the vibration imparted to the cutting head by the crystals when energized will improve the cutting efficiency of the cutter head, but, what is more important, the vibrations will help keep the cutting head from sticking in the artery.

From the foregoing it will be seen that this invention is one well adapted to attain all of the ends and objects hereinabove set forth, together with other advantages that are obvious and that are inherent to the method.

What is claimed is:

1. A catheter for performing an atherectomy procedure to remove plaque from an artery comprising a plaque cutting head including an outer shell of thin flexible material generally cylindrical in cross section and shaped to engage plaque in an artery, said outer shell having a plurality of openings through which the plaque will enter the shell as the shell is forced against the plaque, and a cutter rotating inside the shell to cut the plaque that enters into the shell into small pieces as the catheter is pushed through an artery, an elongated drive shaft for rotating the cutter, piezo electric crystals mounted on the drive shaft to cause the cutting head to vibrate, means for supplying the crystals with electrical energy to cause such vibration, and a motor for rotating the shaft and the cutter.

2. The catheter of claim 1 further provided with a tubular drive shaft and a first elongated tubular member extending through the drive shaft and attached to the outer shell to resist rotation of the outer shell due to counter torque.

3. The catheter of claim 2 further provided with a second elongated tubular member extending over the drive shaft and having an inner diameter larger than the outside diameter of the drive shaft to provide an annular space and means to reduce the pressure in the annular space below ambient pressure to cause the pieces of plaque removed from the artery by the cutter to flow into the annular space along with some blood.

4. The catheter of claim 1 in which the outer shell and cutter are cone-shaped.

5. The catheter of claim 1 in which the cutter includes an outer section positioned to rotate close to the inner surface of the outer shell and having a plurality of openings that move past the openings in the outer shell so that an edge of each opening in the outer section of the cutter will cut off a portion of the plaque extending into the opening in the outer shell.

6. The catheter of claim 5 in which the openings in the outer shell and the outer section of the cutter are position so that not all of the edges of the openings in the cutter are cutting plaque at any one time.

7. The catheter of claims 5 or 6 in which the cutter can be positioned in the outer shell so that all openings in the outer shell are closed.

* * * * *